United States Patent [19]

Kawaki et al.

[11] Patent Number: 4,939,218

[45] Date of Patent: Jul. 3, 1990

[54] SULFUR-CONTAINING ALIPHATIC ACRYLIC COMPOUND, CROSSLINKED POLYMER ARTICLE, AND LENS

[75] Inventors: Takao Kawaki, Tokyo; Makoto Kobayashi, Nagareyama; Osamu Aoki, Matsudo; Yoshie Hiramatsu, Tokyo, all of Japan

[73] Assignee: Mitsubishi Gas Chemical Company, Inc., Tokyo, Japan

[21] Appl. No.: 269,901

[22] Filed: Nov. 10, 1988

[30] Foreign Application Priority Data

Nov. 13, 1987 [JP] Japan .................. 62-285456

[51] Int. Cl.[5] .............................. C08F 28/04
[52] U.S. Cl. ...................... 526/289; 351/159
[58] Field of Search ............... 526/289, 286

[56] References Cited

U.S. PATENT DOCUMENTS 3,716,466  2/1973  Hook .................. 526/289

Primary Examiner—Christopher Henderson
Attorney, Agent, or Firm—Wenderoth, Lind & Ponack

[57] ABSTRACT

A sulfur-containing aliphatic acrylic compound represented by the following general formula [I]

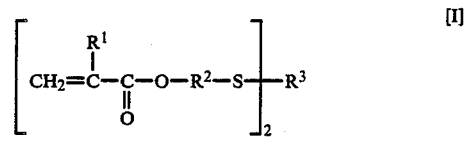

wherein $R^1$ represents a hydrogen atom or a methyl group, $R^2$ represents an aliphatic hydrocarbon group having 1 to 8 carbon atoms, and $R^3$ represents an aliphatic hydrocarbon group having 1 to 8 carbon atoms which may contain oxygen or sulfur in the main chain; a crosslinked polymer article obtained by polymerizing and curing a monomeric mixture composed of 100 to 60% by weight of at least one sulfur-containing aliphatic acrylic compound represented by the general formula [I] and 0 to 40% by weight of another copolymerizable monomer containing an ethylenic bond in a mold together with a radical initiator; a lens composed of the cross-linked polymer article thereof; and a process for producing a crosslinked polymer article thereof.

3 Claims, 2 Drawing Sheets

SULFUR-CONTAINING ALIPHATIC ACRYLIC COMPOUND, CROSSLINKED POLYMER ARTICLE, AND LENS

This invention relates to a novel sulfur-containing aliphatic acrylic compound, a crosslinked polymer article derived from the acrylic compound as a main monomer, and to a lens. More specifically, this invention relates to a novel sulfur-containing aliphatic acrylic compound which can be cast-polymerized to give a cured article having a high refractive index and a high Abbe number.

Organic polymers used for optical lenses include, for example, poly(methyl methacrylate), poly(diethylene glycol bisallyl carbonate), polystyrene and polycarbonate.

Poly(methyl methacrylate) and poly(diethylene glycol bisallyl carbonate) have predominantly been used as lenses for sight correction eyeglasses.

Lenses composed of poly(methyl methacrylate) or poly(diethylene glycol bisallyl carbonate) have a refractive index of as low as about 1.5. To obtain sight correction lenses from these lenses, the thickness of these lenses at their peripheral ends becomes larger than that of an inorganic glass lens.

The demand for weight and thickness reduction has been raised by consumers who need eyeglasses, and to meet this demand, it has been desired to develop transparent organic polymers having a high refractive index.

To develop organic polymers having a high refractive index, various polymers containing a bromophenyl group have been proposed as shown below.

(1) U.S. Pat. No. 4,369,298

This patent describes a "cured resin consisting substantially of a first polymer unit derived from an unsaturated compound having two terminal vinyl groups consisting of bis(alkyleneoxyphenyl)diacrylates or dimethacrylates, bis(alkyleneoxyphenyl)diallyl ethers and bis-(alkyleneoxyphenyl)diallyl carbonates, and a second polymer unit derived from another unsaturated compound radical-polymerizable with the first-mentioned unsaturated compound, said polymer units being bonded to each other at random." This patent document also states: "The aforesaid cured resin can be produced by copolymerizing an intimate mixture consisting substantially of at least one compound selected from the first-mentioned unsaturated compounds having two terminal vinyl groups and prepolymers thereof and at least one compound selected from other unsaturated compounds radical-copolymerizable with the first-mentioned unsaturated compounds and prepolymers thereof in the presence of a radical polymerization initiator. A lens composed of the aforesaid cured resin has a high refractive index, excellent transparency and excellent fire retardancy."

(2) Japanese Laid-Open Patent Publication No. 13321/1984

This patent document states that by reacting a composition composed of the following components A, B and C, a resin having a high refractive index, transparency and antishock properties suitable for plastic lenses can be produced.

A. At least one hydroxyl group-containing vinyl monomer selected from the following (I), (II) and (III).

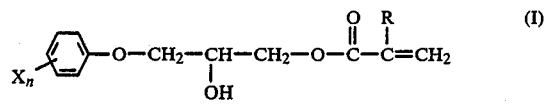

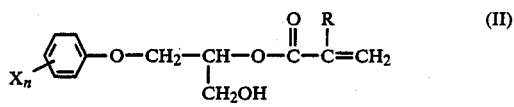

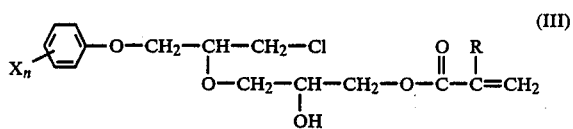

wherein X represents bromine or iodine, R represents a methyl group or a hydrogen atom, and n represents an integer of 1 to 5, B. An isocyanate compound with two or more functional groups, and C. A vinyl monomer.

(3) Japanese Laid-Open Patent Publication No. 11513/1985

This patent document describes a resin composed of a polymer of a composition composed of (A) a mixture or an addition reaction product of (i) an isocyanate compound with two or more functional groups and (ii) a hydroxyl group-containing vinyl monomer of the following formula (I) or (II)

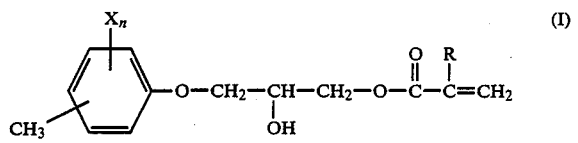

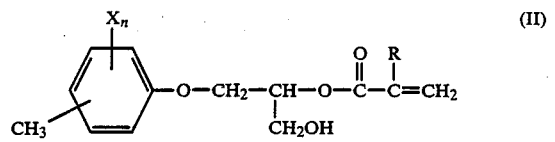

wherein X represents bromine or iodine, R represents a methyl group or a hydrogen atom, and n represents an integer of 1 to 4, and (B) a vinyl monomer, and this resin has a high refractive index, transparency and antishock property suitable for plastic lenses.

(4) Japanese Laid-Open Patent Publication No. 51706/1985

This patent document describes a resin obtained by reacting a (meth)acrylate of the following general formula

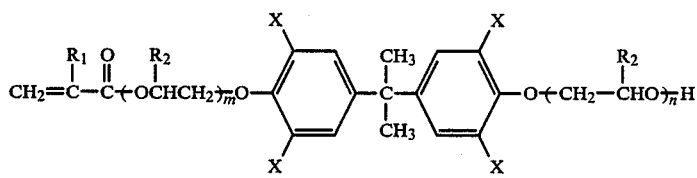

wherein $R_1$ and $R_2$ represent a hydrogen atom or a methyl group, m and n are integers and total of these is 0 to 4, and x represents chlorine, iodine or bromine, and vinyl-polymerizing the resulting urethane (meth)acrylate. It describes that the resin has a high refractive index suitable for plastic lenses.

These resins described in the prior art have considerably improved refractive indices for use as plastic lenses of eyeglasses. The "Abbe number", which is another important factor of plastic lenses, of these resins is only about 30 to 35 which is not fully satisfactory. Another defect of these resins is that since they contain halogens such as bromine, they have unsatisfactory weatherability and their specific gravity is as large as about 1.4.

The "Abbe number" denotes the quantity which defines the dispersibility of light in an optical material and is expressed by the following equation.

$$\text{Abbe number} = \frac{n_D - 1}{n_F - n_C}$$

wherein $n_D$, $n_C$ and $n_F$ are refractive indices for D line (wavelength 589 nm), C line (wavelength 656 nm) and F line (wavelength 486 nm) respectively of Fraunhofer lines.

If the Abbe number of the resin is 40 or more, a lens prepared from it does not permit perception of chromatic aberration over a broad range of degrees from a weak to a strong one.

It is an object of this invention to provide a novel sulfur-containing aliphatic acrylic compound as a monomer capable of giving a polymer having excellent properties for use as a plastic eyeglass lens.

Another object of this invention is to provide a polymer article suitable as a plastic lens having a high refractive index and a high Abbe number.

Still another object of this invention is to provide an industrially advantageous process for production of the aforesaid polymer article.

Yet another object of this invention is to provide a transparent plastic lens having a high refractive index, a high Abbe number and a relatively low specific gravity.

Further objects of this invention will become apparent from the following description.

According to this invention, the above objects are achieved by a sulfur-containing aliphatic acrylic compound represented by the following general formula [I]

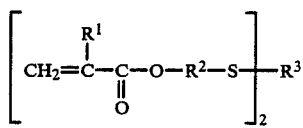

wherein $R^1$ represents a hydrogen atom or a methyl group, $R^2$ represents an aliphatic hydrocarbon group having 1 to 8 carbon atoms, and $R^3$ represents an aliphatic hydrocarbon group having 1 to 8 carbon atoms which may contain oxygen or sulfur in the main chain; and a crosslinked polymer article obtained by bulk polymerization of a monomeric mixture composed of 100 to 60% by weight of at least one sulfur-containing aliphatic acrylic compound of general formula [I] above and 0 to 40% by weight of another copolymerizable monomer containing an ethylenic bond in a mold together with a radical polymerization initiator.

The present invention will now be described in detail.

Sulfur-containing aliphatic acrylic compound [I] and process for production thereof The sulfur-containing aliphatic acrylic compound of this invention is represented by general formula [I].

In general formula [I], $R^1$ represents a hydrogen atom or a methyl group.

$R^2$ represents an aliphatic hydrocarbon group having 1 to 8 carbon atoms, preferably a saturated aliphatic hydrocarbon group having 1 to 8, particularly 1 to 4, carbon atoms. Specific examples are —CH$_2$—, —CH$_2$CH$_2$—, —CH$_2$CH$_2$CH$_2$—, and —CH$_2$CH$_2$CH$_2$CH$_2$—. —CH$_2$CH$_2$— is especially preferred.

$R^3$ represents an aliphatic hydrocarbon having 1 to 8 carbon atoms, preferably 1 to 4 carbon atoms, which may contain oxygen or sulfur in the main chain. Preferably, the aliphatic hydrocarbon is a saturated aliphatic hydrocarbon. Specific examples of preferred $R^3$ groups are —CH$_2$—, —CH$_2$CH$_2$—, —CH$_2$CH$_2$CH$_2$—, —CH$_2$CH$_2$CH$_2$CH$_2$—, —CH$_2$CH$_2$SCH$_2$CH$_2$— and —CH$_2$CH$_2$OCH$_2$CH$_2$—. —CH$_2$—, —CH$_2$CH$_2$— and —CH$_2$CH$_2$SCH$_2$CH$_2$— are especially preferred.

Specific examples of the sulfur-containing aliphatic acrylic compound represented by general formula [I] are shown below. These are merely illustrative, and are not intended in any way to limit the invention thereby.

(1) Dimethacryloyloxyethylthiomethane,
(2) diacryloyloxyethylthiomethane,
(3) 1,2-bis(methacryloyloxyethylthio)ethane,
(4) 1,2-bis(acryloyloxyethylthio)ethane,
(5) 1,3-bis(methacryloyloxyethylthio)propane,
(6) 1,3-bis(acryloyloxyethylthio)propane,
(7) 1,4-bis(methacryloyloxyethylthio)butane,
(8) 1,4-bis(acryloyloxyethylthio)butane,
(9) bis(2-methacryloyloxyethylthioethyl)sulfide,
(10) bis(2-acryloyloxyethylthioethyl)sulfide,
(11) bis(2-methacryloyloxyethylthioethyl)ether, and
(12) bis(2-acryloyloxyethylthioethyl)ether.

The sulfur-containing aliphatic acrylic compound of general formula [I] can be produced by reacting a diol compound represented by the following general formula [II]

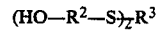

wherein $R^2$ and $R^3$ are as defined with regard to general formula [I], with an acrylic compound represented by the following general formula [III]

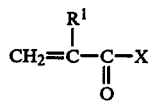

[III]

wherein $R^1$ represents a hydrogen atom or a methyl group and X represents chlorine or —OH.

When (meth)acrylic acid (X=—OH) is used as the acrylic compound of general formula [III], the above process is carried out, for example, by reacting 2 to 6 moles of (meth)acrylic acid with 1 mole of the diol compound of general formula [II] in a hydrocarbon solvent such as benzene or toluene. Advantageously, the reaction is carried out using 0.01 to 0.5 mole, per mole of the diol compound, of a catalyst, for example a mineral acid such as sulfuric acid or hydrochloric acid, or an organic acid such as p-toluenesulfonic acid. Desirably, the reaction is carried out at a temperature of 80° to 120° C. while the water formed is removed out of the system by azeotropic distillation.

When (meth)acryloyl chloride (X=Cl) is used as the acrylic compound of general formula [III], the process may be carried out by reacting 2 to 6 moles of (meth)acryloyl chloride with 1 mole of the diol compound of general formula [II] together with 2 to 6 moles of an organic base such as triethylamine or pyridine. The reaction may be carried out in a solvent, preferably acetone, methyl ethyl ketone, dioxane, tetrahydrofuran, or chloroform. Desirably, the reaction is carried out at a temperature of −10° to 50° C., preferably −10° to 30° C.

Preparation of a starting mixture

In the present invention, a crosslinked polymer can be obtained by bulk polymerization of the sulfur-containing aliphatic acrylic compound of general formula [I] (to be referred to as an "acrylic monomer") as a main monomer. At least one acrylic monomer of general formula [I] may be used as the starting material. A mixture of at least one acrylic monomer with another radical-polymerizable monomer containing an ethylenic bond (to be referred to as "comonomer") may also be used as the starting material.

The proportions of the acrylic monomer and the comonomer in the mixture are determined depending upon the type of the acrylic monomer, the type of the comonomer, the properties and use of the desired crosslinked polymer to be obtained, and economy. It is advantageous to use a monomeric mixture containing 100 to 60% by weight, preferably 100 to 70% by weight, of the acrylic monomer and 0 to 40% by weight, preferably 0 to 30% by weight, of the comonomer.

The comonomer is a radical-polymerizable monomer containing an ethylenic bond which copolymerizes with the acrylic monomer of general formula [I] in bulk to give a crosslinked polymer, preferably a vinyl compound, an acrylic compound or an allyl compound.

Specific examples of the comonomer are vinyl compounds such as styrene, chlorostyrene and divinylbenzene, acrylic compounds such as methyl (meth)acrylate, dicyclopentenyl (meth)acrylate, cyclohexyl (meth)acrylate, phenyl (meth)acrylate, benzyl (meth)acrylate and chlorphenyl (meth)acrylate, and allyl compounds such as diallyl phthalate and diethylene glycol bisallyl carbonate. Preferred among these comonomers are styrene, chlorostyrene, divinylbenzene, phenyl (meth)acrylate, benzyl (meth)acrylate and diallyl phthalate.

According to this invention, a starting mixture is prepared from the acrylic monomer of general formula [I] or the mixture of the acrylic monomer and the comonomer and a radical polymerization initiator. By bulk polymerization of the starting mixture in a mold, a crosslinked polymer article can be obtained.

A compound which is decomposed by the action of heat and/or light to generate radicals is used as the radical polymerization initiator. Compounds generally known as radical polymerization initiators for the polymerization of vinyl compounds and allyl compounds are preferably used in this invention.

Examples of the radical polymerization initiator include azo compounds and peroxides, specifically benzoyl peroxide (BPO), diisopropyl peroxycarbonate, azobisisobutyronitrile, di-t-butyl peroxide, cumene hydroperoxide, $H_2O_2$, potassium persulfate and ammonium persulfate. Curing may also be effected by ultraviolet light using a photosensitizer such as benzophenone, benzoin or benzoin methyl ether. These radical polymerization initiators may be used singly or in combination.

The amount of the radical polymerization initiator is usually 0.01 to 5 parts by weight, preferably 0.1 to 3 parts by weight, per 100 parts by weight of the monomeric mixture.

A promoter for accelerating decomposition may be used together with the radical polymerization initiator. Known promoters may be used, and examples include primary, secondary or tertiary amines, metal salts and metal complexes.

In the preparation of the crosslinked polymer article by this invention, additives which are desired to be incorporated in the resulting polymer should be added in advance to the starting mixture. The additives may be those which are generally used as additives to polymers, and include, for example, stabilizers, ultraviolet absorbers, coloration inhibitors, antioxidants, pigments and fire retardants.

Crosslinked polymer article and its production

The crosslinked polymer article in accordance with this invention may be produced by (a) preparing a starting mixture from a monomeric mixture composed of 100 to 60% by weight of at least one sulfur-containing aliphatic acrylic compound (acrylic monomer) represented by general formula [I] and 0 to 40% by weight of another copolymerizable monomer containing an ethylenic bond (comonomer), and a radical polymerization initiator, (b) feeding the starting mixture into a mold, (c) heating the starting mixture in the mold to form a crosslinked polymer article, and then (d) withdrawing the resulting polymer article from the mold.

Thus, according to this invention, the starting mixture containing the radical polymerization initiator is fed into the mold, and heated and/or irradiated with ultraviolet light to thereby generate radicals and polymerize the monomeric mixture in the mold. As a result, the monomeric mixture polymerizes in bulk in the mold and a cured polymer article of a three-dimensional network structure is formed.

The starting mixture of this invention may be directly fed into the mold. If desired, prior thereto, the mixture may be subjected to preliminary polymerization. The preliminary polymerization may be effected by heating the starting mixture for a short period of time to an extent such that the mixture does not lose flowability. The preliminary polymerization is frequently effective because it can prevent occurrence of raisings and depressions or cracking on the surface of the molded article which is due to an abrupt reaction occurring in the mold.

At room temperature, the starting mixture to be fed into the mold usually has flowability and does not start to polymerize. But when the starting mixture is fed into the mold, and the mold is heated, or irradiated with ultraviolet light, or heated and simultaneously irradiated with ultraviolet light, the polymerization reaction of the monomeric mixture starts to proceed. Heating the mold is a preferred embodiment of performing the polymerization because the equipment is simple, the polymerization reaction can be easily controlled, and the method is economical.

The temperature at which the mold is heated is in the range of 40° to 130° C., preferably 40° to 120° C. It is not always necessary to heat the mold at a fixed temperature. Investigations of the present inventors have shown that a polymer article having excellent properties as a lens can be obtained by heating the mold such that the polymerization is started at relatively low temperatures within the above-specified range, and the rate of temperature elevation is accelerated as the temperature becomes higher. The heating time is usually at least 1 hour, preferably at least 5 hours. The upper limit of the heating time is 24 hours, preferably 20 hours.

The shape of the mold depends upon the shape of the desired molded article. For example, for preparation of an optical lens, the mold may be of a simple structure composed of two glass sheets and an O-ring interposed between them.

After the polymerization and curing have been completed in the mold, the molded article is withdrawn from the mold. The molded article so withdrawn may be directly used as a product, or submitted to the next step. As required, the molded article may be heat-treated for post cure.

Because the crosslinked polymer article obtained by the present invention has a high refractive index and an Abbe number of at least 40 and is transparent, it has very good properties for use as a lens for sight-correcting eyeglasses. Furthermore, the resulting molded article shows excellent thermal resistance, impact strength, processability, chemical resistance and dyeability, and therefore, has a very high utilitarian value as an optical lens, as can be seen from examples given below.

The following Examples specifically illustrate the present invention. In these examples, all parts are by weight.

EXAMPLE 1

A 1-liter four-necked flask equipped with a stirrer, a thermometer, a dropping funnel and a condenser was charged with 36.4 parts of 1,2-bis(2-hydroxyethylthio)ethane, 44.4 parts of triethylamine and 300 parts of tetrahydrofuran, and with stirring, 39.8 parts of acryloyl chloride was added dropwise while maintaining the mixture at below 10° C. After the addition, the mixture was stirred continuously for 2 hours.

The salt was separated by filtration from the reaction mixture. The residue was concentrated under reduced pressure at 40° C. to remove tetrahydrofuran. The residue was mixed with 500 ml of benzene, and transferred to a separating funnel. The mixture was washed with 500 ml of a 1N aqueous solution of NaOH four times, and then further washed with water until it became neutral.

Figure 1:
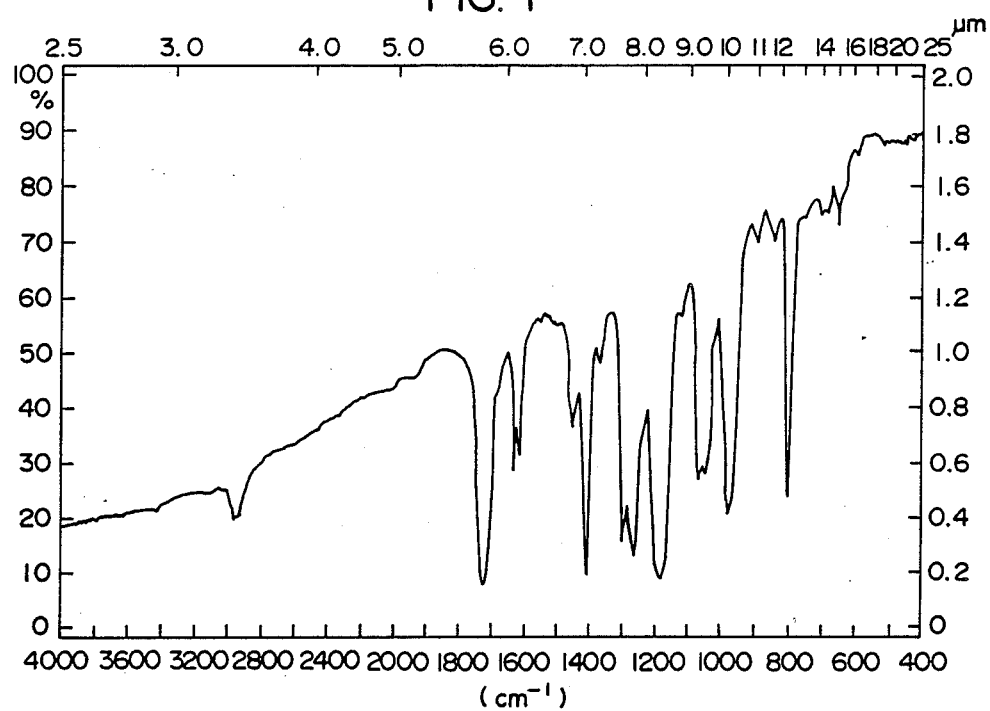
FIGS. 1 and 2 respectively show the infrared absorption spectrum (FIG. 1) and the NMR spectrum (FIG. 2) of 1,2-bis(acryloyloxyethylthio)ethane obtained in Example 1.
Figure 2:
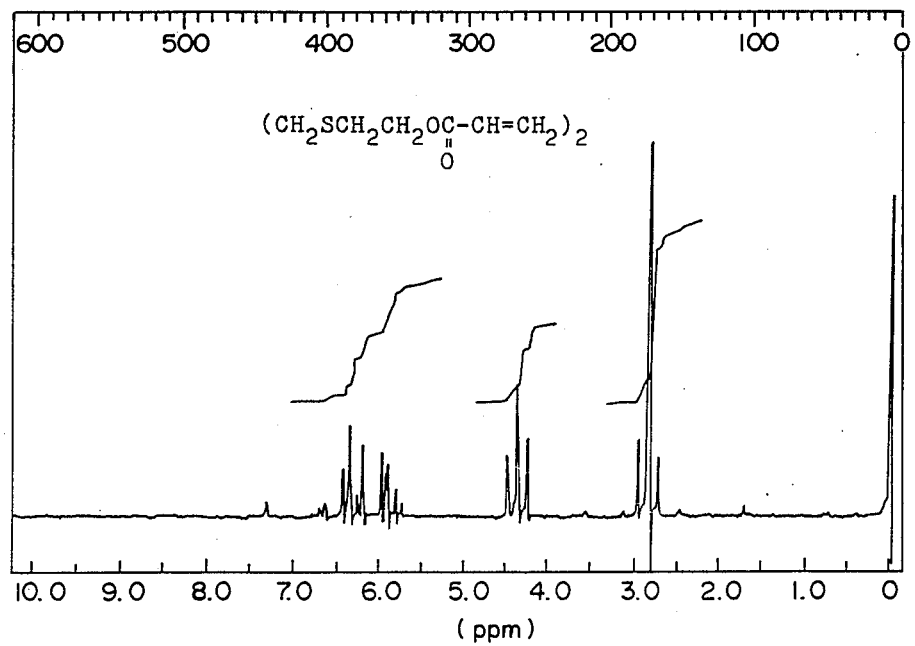

The product was decolorized with silica gel, and the solvent was removed under reduced pressure at 50° C. to give 1,2-bis(acryloyloxyethylthio)ethane. The infrared absorption spectrum and the NMR spectrum of this product are shown in FIGS. 1 and 2, respectively.

EXAMPLE 2

A mixture of 100 parts of 1,2-bis(acryloyloxyethylthio)ethane obtained in Example 1 and 0.5 part of perbutyl O[t-butylperoxy(2-ethylhexanoate)] was poured into a mold composed of two glass sheets and an O-ring interposed between them, and polymerized in accordance with the following program. Specifically, after the mixture was poured into the mold, the temperature was raised linearly from 50° C. to 55° C. over 10 hours, from 55° to 65° C. over 5 hours, from 65° to 75° C. over 2 hours, and from 75° to 100° C. over 3 hours. The mixture was then maintained at 100° C. for 1 hour to perform polymerization.

The resulting cured product was colorless and transparent. It had a refractive index, measured by an Abbe refractometer, of 1.575 (20° C.), an Abbe number of 46.4 (20° C.), and a specific gravity at room temperature of 1.32.

EXAMPLES 3-4

The 1,2-bis(acryloyloxyethylthio)ethane obtained in Example 1 and styrene were mixed in the proportions shown in Table 1, and polymerized as in Example 2. The resulting cured polymer articles were colorless and transparent and had the properties shown in Table 1.

TABLE 1

|  | Example 3 | Example 4 |
| --- | --- | --- |
| 1,2-bis(acryloyloxy-ethylthio)ethane | 85 parts | 70 parts |
| Styrene | 15 parts | 30 parts |
| Refractive index (20° C.) | 1.578 | 1.581 |
| Abbe number (20° C.) | 42.6 | 40.5 |
| Specific gravity (room temperature) | 1.27 | 1.23 |

EXAMPLE 5

Figure 3:
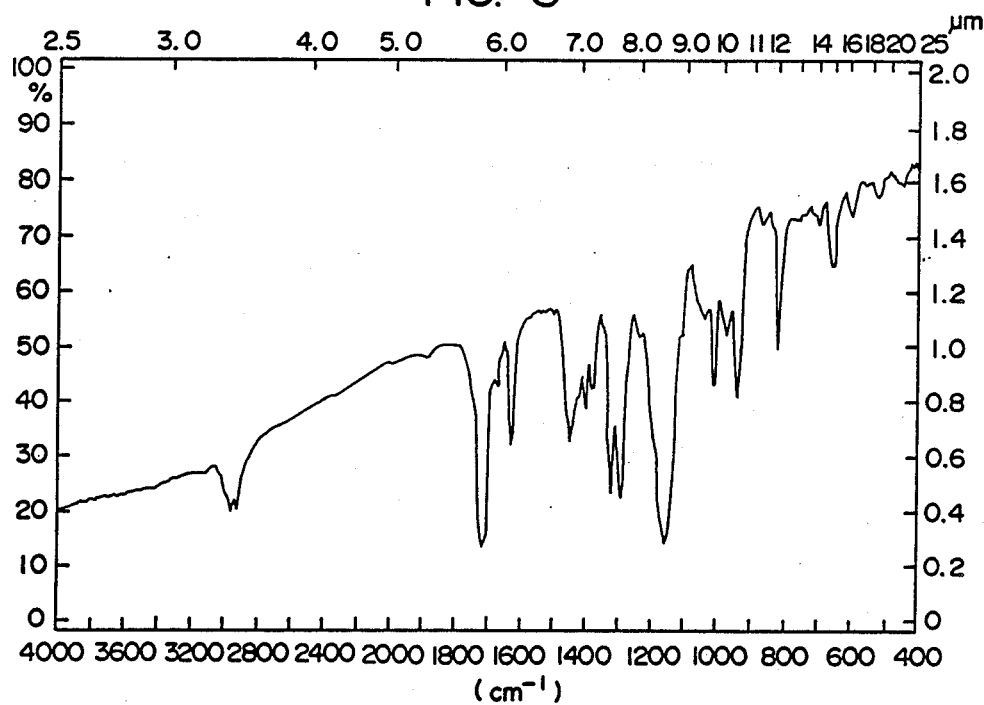
FIGS. 3 and 4 respectively show the infrared absorption spectrum (FIG. 3) and the NMR spectrum (FIG. 4) of 1,2-bis(methacryloyloxyethylthio)ethane obtained in Example 5.
Figure 4:
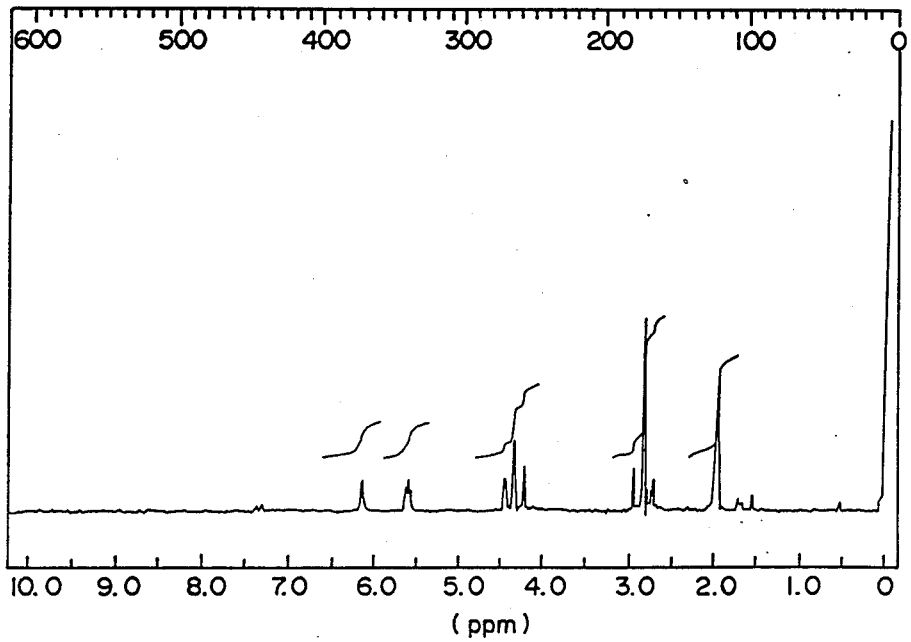

Example 1 was repeated except that 46.0 parts of methacryloyl chloride was used instead of 39.8 parts of acryloyl chloride. The infrared absorption spectrum and the NMR spectrum of the resulting 1,2-bis(methacryloyloxyethylthio)ethane are shown in FIGS. 3 and 4, respectively.

EXAMPLE 6

A mixture composed of 100 parts by weight of the 1,2-bis(methacryloyloxyethylthio)ethane obtained in Example 5 and 0.5 part of perbutyl O[t-butylperoxy(2- ethylhexanoate)] was polymerized and molded as in Example 2. The resulting cured article was colorless and transparent, and had a refractive index of 1.568 (20° C.), an Abbe number of 45.8 (20° C.) and a specific gravity at room temperature of 1.28.

EXAMPLE 7

The molded articles obtained in Examples 2, 3, 4 and 6 were tested for the following properties.

(1) Thermal resistance

The Vicat heat softening temperature of the cured article under a load of 1 kg was measured. When it had a Vicat heat softening temperature of 120° C. or higher, the cured article had good thermal resistance.

(2) Impact strength

A disc-like sample, 60 mm in diameter and 2.0 mm in thickness, of the cured article was prepared. An iron ball weighing 30 g was let fall onto the disc sample from a height of 1.27 m. When the sample was not broken, the sample had good impact strength.

(3) Processability

The cured article was ground by a lens grinder. When the ground surface was good, the cured article had good processability.

(4) Chemical resistance

The cured article was immersed in methanol or acetone for 3 minutes. When there was no change in the article, the article had good chemical resistance.

(5) Dyeability

A bath of a red color disperse dye, a blue color disperse dye and a yellow color disperse dye was prepared. While the temperature of the bath was maintained at 93° C., the cured article was immersed in it for 10 minutes to perform dyeing. When the cured article was dyed to brown having a total light transmittance of 50%, the cured article had good dyeability.

The cured articles obtained in Examples 2, 3, 4 and 6 all satisfied the testing standards and showed good properties (1) to (5).

We claim:

1. A crosslinked polymer article obtained by polymerizing and curing a monomeric mixture composed of 100 to 60% by weight of at least one sulfur-containing aliphatic acrylic compound represented by formula [I]

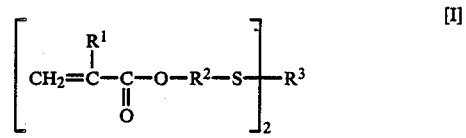

wherein $R^1$ represents a hydrogen atom or a methyl group, $R^2$ represents an aliphatic hydrocarbon group having 1 to 8 carbon atoms, and $R^3$ represents an aliphatic hydrocarbon group having 1 to 8 carbon atoms which may contain oxygen or sulfur in the main chain, and 0 to 40% by weight of at least one copolymerizable monomer selected from the group consisting of radical-polymerizable vinyl compounds, acrylic compounds and allyl compounds, in a mold together with a radical initiator.

2. The crosslinked polymer article of claim 1 in which the radical initiator is at least one compound selected from peroxides, azo compounds and photosensitizers.

3. A lens composed of the crosslinked polymer article of claim 1.

* * * * *